United States Patent

Pourprix

Patent Number: 5,620,100
Date of Patent: Apr. 15, 1997

[54] CHARGED PARTICLE SELECTOR

[75] Inventor: Michel Pourprix, Montlhéry, France

[73] Assignee: Commissariat a l'Energie Atomique, Paris, France

[21] Appl. No.: 438,704

[22] Filed: May 11, 1995

[30] Foreign Application Priority Data

May 24, 1994 [FR] France .................................. 94 06273

[51] Int. Cl.⁶ ......................................................... B03C 7/00
[52] U.S. Cl. ..................... 209/127.1; 209/127.4
[58] Field of Search ................................. 209/127.1, 131, 209/128, 636, 212, 213, 214, 638, 127.4

[56] References Cited

U.S. PATENT DOCUMENTS

| 3,953,792 | 4/1976 | Fletcher et al. .................. 209/127.1 X |
| 4,556,849 | 12/1985 | Kalakutsky et al. . |
| 5,117,190 | 5/1992 | Pourprix . |
| 5,454,472 | 10/1995 | Benecke et al. ..................... 209/127.1 |

FOREIGN PATENT DOCUMENTS 0404681  12/1990  European Pat. Off. .
93/07465  4/1993  WIPO .

OTHER PUBLICATIONS

Transactions of the IEEE on Nuclear Science, vol. NS-19, No. 1, Feb. 1, 1972, pp. 64–74, Raabe, "Instruments And Methods For Characterizing Radioactive Aerosols' Electrostatic Samplers". pp. 66–67.

Database WPI, Week 8440, Nov. 14, 1984, Derwent Publications Ltd., London, GB; AN 84–248832 & SU-A-1 071 947 (Len.Aviation Inst.) Feb. 7, 1984.

Aerosol Science and Technology, vol. 13, Oct. 1, 1990, pp. 230–240, Wang et al., "Scanning Electrical Mobility Spectrometer"., pp. 232–235.

Journal of Aerosol Science, vol. 6, Dec. 1, 1975, pp. 443–451, Knutson et al., "Aerosol Classification By Electric Mobility, Etc.".

Review of Scientific Instruments, vol. 51, No. 8, Aug. 1, 1980, pp. 1098–1104, Schowengerth et al., "A Parallel Plate Electrostatic Size Classifier, Etc.".

Primary Examiner—D. Glenn Dayoan
Attorney, Agent, or Firm—Pearne, Gordon, McCoy & Granger

[57] ABSTRACT

The electrostatic selector of aerosol particles of an atmosphere has a first (18) and a second (20) spaced, parallel, coaxial conductive disks between which is established an electrical field, an annular slot (22) made in the first disk in order to communicate with the atmosphere to be examined, a central intake (26) for bringing about a circulation from the periphery of the disks of a stable, centripetal, laminar filtered air flow, the second disk (20) having a central extraction orifice (28).

4 Claims, 1 Drawing Sheet

CHARGED PARTICLE SELECTOR

TECHNICAL FIELD

The present invention relates to a charged particle electrical mobility selector more particularly used in the case of fine particles for selecting particles having a given grain size (monodisperse aerosol) from particles of a random grain size (polydisperse aerosol), which are suspended in air or another gas.

Among other applications this type of apparatus is e.g. particularly suitable for use in the field of aerosol research, particularly for producing calibrated particles or for studying the electrical charge of the aerosols. It is more especially suitable for submicron aerosols down to the smallest aerosol sizes, i.e. approximately 1 nanometer ($10^{-9}$ m).

PRIOR ART

One of the most frequently used means for selecting monodisperse particles is based on the fact that aerosols are carriers of electrical charges equal to the unitary electrical charge or a multiple thereof.

Consequently for the selection of charged particles suspended in a gas use has already been made of electrostatic fields acting on the electrical charges which they carry. In this connection there is currently a definition of a fundamental notion in this field, which is that of the electrical mobility of a charged particle placed in an electrostatic field. This quantity, which defines the largest or smallest aptitude of such a particle to undergo a deviation under the effect of said field can be represented by the following equation:

$$\vec{W} = Z\vec{E}$$

in which $\vec{W}$ is the drift velocity acquired by the particle under the influence of the electrical field $\vec{E}$ to which it is exposed. The proportionality coefficient Z between the two aforementioned quantities is the electrical mobility in question. This electrical mobility is on the one hand proportional to the electrical charge of the particle and on the other inversely proportional to its diameter, so that it is possible to produce true selectors of particles as a function of their electrical mobility consisting of subjecting particles entrained in a gaseous flow to the action of an electrical field between two electrodes. Under the effect of the field, the charged particles are deposited, as a function of their sign, on one of these electrodes and the abscissa of their deposition with respect to the direction of the gaseous flow is characteristic of their mobility in the sense that the higher said mobility, the more the abscissa of their deposition is close to the origin of the gaseous flow carrying the same. This leads to a spread or separation in space of the collected particles. Following said separation, it is possible to select the particles having a certain mobility, i.e. a certain grain size if the charge law is known.

An apparatus based on this principle is described in French certificate of addition 90 02413 of 27.2.1990, published under No. 2 658 916 (U.S. Pat. No. 5,117,190) and entitled "Electrostatic aerosol particle sensor and equipments incorporating this application". This type of apparatus is illustrated in FIG. 1 and has two spaced, parallel, coaxial conductive disks 2, 4 between which is established a potential difference V and therefore an electrical field $\vec{E}$. The disk 2 has an annular slot 6 (radius $r_1$) by means of which are introduced the particles of an aerosol at a rate $q_1$. A central intake 8 is provided by means of which an air flow Q circulates under the effect of a not shown pump.

The particles are entrained to a second annular slot 10 of radius $r_2$ formed in the disk 4 under the combined action of a filtered air flow at the rate $q_0$, which is radial and laminar and established between the two disks, as well as the electrical field E imposed between the two disks.

Through the slot 10, the air flows at a rate $q_2$ into a cylindrical box 12 fixed beneath the disk 4 giving $Q=q_0+q_1-q_2$. The particles traversing the slot 10 have the same electrical mobility $Z=Q/\pi E(r_1^2-r_2^2)$. For information, the order of magnitude of the flow rates is $q_1=q_2=Q/10$.

In order to regulate this electrical mobility to the desired value for each individual case, it is possible to act on two parameters, namely the flow rate Q on the one hand and the potential difference V applied between the two coaxial conductive disks 2 and 4 on the other.

By means of the cylindrical box 12 and a pipe 14, the particles can then be directed towards any type of device appropriate for the envisaged application, e.g. a particle counter to be calibrated with the thus produced, fine, calibrated particles.

This type of apparatus, like all known charged particle selectors, suffers from certain disadvantages if it is used for selecting particles having a nanometric size.

Firstly, the transport of such particles in circuits of the system leads to losses as a result of Brown scatter in the vicinity of the walls, particularly in the cylindrical box 12.

Moreover, the transit time in this box, which can be considerable, is not the same for all the particles and consequently there is a certain scatter through the apparatus, which can be prejudicial in certain applications.

DESCRIPTION OF THE INVENTION

The invention aims at solving these problems.

It relates to a selector of aerosol particles contained in an atmosphere comprising a first and a second spaced, parallel, coaxial conductive disks between which it is possible to establish an electrical field by raising them to different potentials, the space between the two disks communicating with the atmosphere to be examined through an annular slot of radius $r_1$ made in the first disk, a central intake being provided in the first disk for bringing about the circulation in said space, from the periphery of the disk, of a stable, centripetal, laminar filtered air flow, characterized in that the second disk has a central extraction orifice.

By means of said central orifice, it is possible to select aerosol particles having a clearly defined electrical mobility.

In addition, compared with known apparatuses, said central extraction device is easy to produce, whilst guaranteeing better performance characteristics, with in particular less fine particle losses and a shorter transit time in the extraction circuit.

Other embodiments of the invention can be gathered from the dependent claims.

BRIEF DESCRIPTION OF THE DRAWINGS

The features and advantages of the invention can be better gathered from the following description of non-limitative embodiments and with reference to the attached drawings, wherein show:

FIG. 1 A prior art aerosol particle selector.

FIGS. 2 and 3 The principle of a particle selector according to the invention.

DETAILED DESCRIPTION OF EMBODIMENTS

Figure 1:
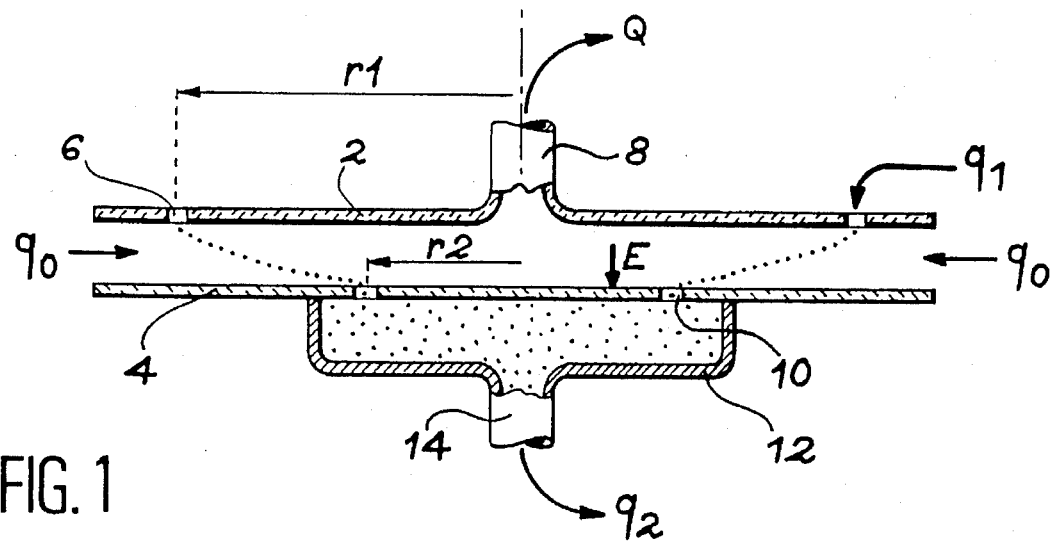
Figure 2:
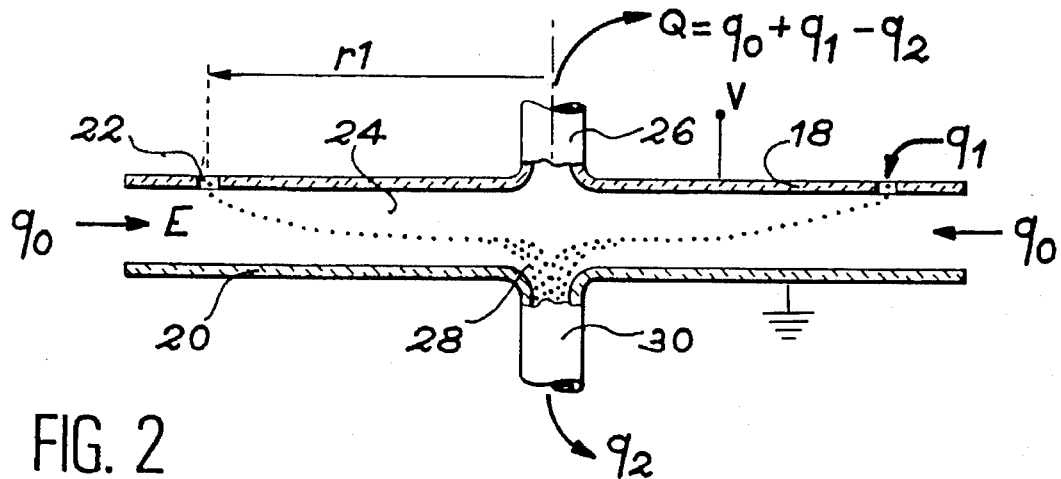
Figure 3:
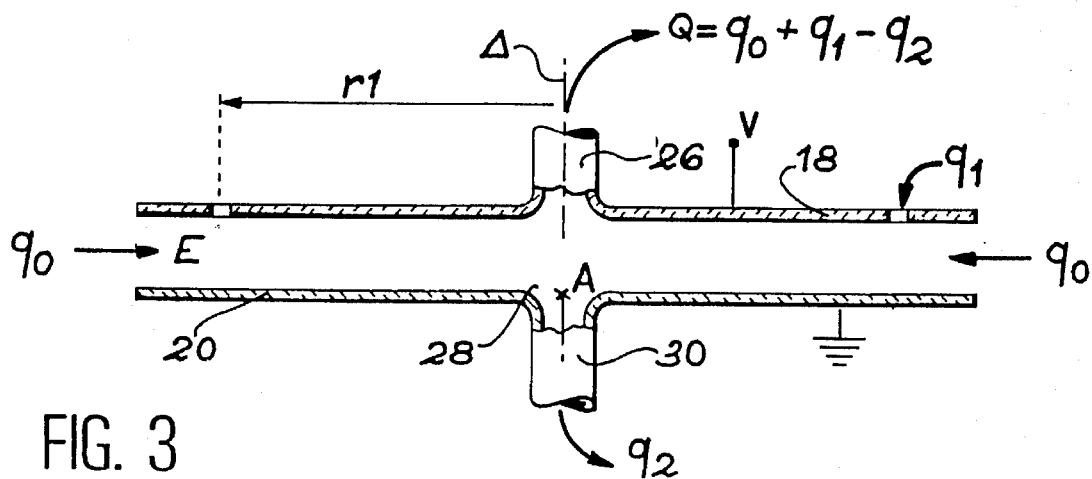

FIG. 2 is a diagram of a selector according to the invention. The apparatus comprises two concentric disk 18, 20. The first disk 18 has an annular slot 22 of radius $r_1$ by means of which a gas sample containing the particles to be selected is introduced with a flow rate $q_1$. As the two disks are conductive, each of them can be raised to a certain potential and an electrical field $\vec{E}$ is established in the space 24 separating them. In the second disk 20 is made a central, circular orifice 28 to be traversed by an air flow $q_2$. Between the two disks, onto the periphery of the space 24 and using means not shown in FIG. 2, is injected an entrainment gas (filtered air), $q_o$, so that a laminar flow circulates between the two disks, up to the central suction pipe 26, which consequently absorbs a flow $Q=q_0+q_1-q_2$. The selected particles can then be discharged by a pipe 30 to the outside of the selector.

The central extraction orifice 28 represents a vital point both from the aeraulic standpoint and from the electrical standpoint, as illustrated in FIG. 3.

If it is firstly assumed that there is no extraction orifice 28, it is then possible to define a point A at the intersection of the central axis $\Delta$ of the apparatus and the disk 20. This point A is a vital aeraulic point because it corresponds to the stoppage point of the laminar flow. It is also a vital point from the electrical standpoint, because the field lines are poorly defined at this location, whereas they are perfectly defined between the two disks elsewhere (except on their periphery, but this has no influence because there are no aerosol particles).

Therefore the basis for the provision of an extraction orifice 28 at point A is not particularly obvious. However, it has been found that this configuration makes it possible to select aerosol particles with a clearly defined electrical mobility given by $Z=Q/\pi E r_1^2$.

The diameter ø of the orifice 28 is preferably chosen so as to ensure a good selectivity of the particles (if the diameter is large the selectivity is low), but also so as not to disturb the flow of fluid traversing it (if the diameter is small, there can be an excessive pressure drop at said orifice).

The particles extracted from the selector can then be counted by a detector chosen from among known systems usually based on optical or electrical methods.

The described apparatus has as its essential application the production of monodisperse particles from polydisperse sources in the submicron particle range. In order to produce particles of a given size, it is merely necessary to select them as a function of the mobility Z corresponding to said size and therefore choose the appropriate field E and flow rate Q.

I claim:

1. Electrical mobility selector of charged aerosol particles contained in an atmosphere to be examined comprising a first and a second, spaced, parallel, coaxial conductive disks; means for establishing an electrical field E between said disks by raising the disks to different potentials; an annular slot of radius $r_1$ in the first disk, the space between the two disks communicating with the atmosphere to be examined through the annular slot; a central intake provided in the first disk for bringing about the circulation in said space, from the periphery of the disk, of a stable, centripetal, laminar filtered air flow; and a central extraction orifice in the second disk.

2. Selector according to claim 1, further comprising a pipe fixed to the second disk, the particles being discharged to the outside of the selector by said pipe.

3. Selector according to one of the claims 1 or 2, wherein the diameter of the central extraction orifice is chosen so as to ensure the selectivity of the particles.

4. Electrical mobility selector of charged aerosol particles contained in an atmosphere to be examined comprising a first and a second, spaced, parallel, coaxial conductive disks; means for establishing an electrical field E between said disks by raising the disks to different potentials; an annular slot of radius $r_1$ in the first disk, the space between the two disks communicating with the atmosphere to be examined through the annular slot; a central intake provided in the first disk for bringing about the circulation in said space, from the periphery of the disk, of a stable, centripetal, laminar filtered air flow; and a central extraction orifice in the second disk having a diameter so as to ensure selectivity of the particles.

* * * * *